United States Patent [19]

Anderson, deceased et al.

[11] Patent Number: 4,929,562

[45] Date of Patent: * May 29, 1990

[54] METHOD AND APPARATUS FOR DETECTING GEM-POLYHALOGENATED HYDROCARBONS

[75] Inventors: William G. Anderson, deceased, late of Livermore; Johanna S. Anderson, legal representative, Palm Springs, both of Calif.

[73] Assignee: The Regents of the University of California, Berkeley, Calif.

[*] Notice: The portion of the term of this patent subsequent to Dec. 29, 2005 has been disclaimed.

[21] Appl. No.: 898,078

[22] Filed: Aug. 20, 1986

[51] Int. Cl.$^5$ .................. G01N 33/48; G01N 21/78
[52] U.S. Cl. ...................... 436/126; 436/164; 436/167; 436/172; 422/82.07; 422/58
[58] Field of Search ............. 436/124–126, 436/163–168, 172, 112; 422/68, 58

[56] References Cited

U.S. PATENT DOCUMENTS

| | | | |
|---|---|---|---|
| 3,275,416 | 9/1966 | Zaar et al. | 436/165 |
| 3,472,626 | 10/1969 | Law | 436/126 |
| 3,506,828 | 4/1970 | Hansen et al. | 436/183 |
| 3,528,931 | 9/1970 | Dunn, Jr. et al. | 436/164 |
| 3,690,769 | 9/1972 | Mori | 128/633 |
| 3,741,727 | 6/1973 | Stroterhoff | 422/58 |
| 3,814,081 | 6/1974 | Mori | 128/634 |
| 3,816,533 | 6/1974 | Brandstrom et al. | 436/126 |
| 3,873,271 | 3/1975 | Young et al. | 436/165 |
| 3,984,204 | 10/1976 | Jenkins et al. | 422/58 |
| 4,150,233 | 4/1979 | Chadwick | 436/124 |
| 4,200,110 | 4/1980 | Peterson et al. | 128/634 |
| 4,201,222 | 5/1980 | Haase | 128/634 |
| 4,476,870 | 10/1984 | Peterson et al. | 128/634 |
| 4,509,370 | 4/1985 | Hirschfeld | 73/705 |
| 4,560,248 | 12/1985 | Cramp et al. | 128/633 |

OTHER PUBLICATIONS

T. Uno et al., "Chem. Pharm. Bull.", vol. 30, p. 1876, (1982).

*Primary Examiner*—Barry S. Richman
*Assistant Examiner*—Timothy M. McMahon
*Attorney, Agent, or Firm*—Stephen C. Macevicz; Henry P. Sartorio

[57] ABSTRACT

A method and optrode for detecting gem polyhalogenated hydrocarbons in a sample fluid based on a single phase Fujiwara reaction as provided. The method comprises contacting a reaction mixture with a sample fluid which contains the gem-polyhalogenated hydrocarbons. The reaction mixture comprises an aqueous solution of pyridine or derivative thereof and a hindered nitrogen base. Upon contact a fluorescent and/or chromgenic reaction product forms whose fluorescence and/or absorbance is related to the concentration of gem-polyhalogenated hydrocarbons in the sample fluid.

20 Claims, 4 Drawing Sheets

METHOD AND APPARATUS FOR DETECTING GEM-POLYHALOGENATED HYDROCARBONS

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

The invention relates generally to the detection of halogenated hydrocarbons, and more particularly to the fluorometric and/or colorimetric detection of gem-polyhalogenated hydrocarbons.

Organohalogens are used extensively in medicine, industry, and agriculture worldwide. Some classes of these compounds are known to be carcinogenic, teratogenic, or otherwise toxic. Because of their widespread use and pervasiveness in the environment, concern has arisen as to the possible deleterious effects that unintended exposure to them might have on human health, Horvath, *Halogenated Hydrocarbons* (Marcel Dekker, Inc., New York, 1982).

The industrial and commercial applications of organohalogen compounds are almost innumerable. They are used as solvents for the extraction of natural products, dry cleaning fluids, degreasing agents, fuel additives, fumigants, and intermediates for the synthesis of a multitude of other organic compounds. Polychlorobiphenyls (PCBs) are used as dielectric fluids in the construction of transformers, and chlorofluorocarbons are used as refrigerants and also as aerosol propellants, for the dispersal of a multitude of household products. Many of these compounds are known carcinogens, Kraybill, et al. Eds, *Environmental Cancer* (John Wiley & Sons, New York, 1977).

Chloroform, first synthesized in 1831, was used as a general anesthetic in 1847, and it and other organic compounds provided the sedation and relief from pain needed for the development of modern surgery. Chloroform has now been replaced by safer and more effective halogen relatives such as halothane, methoxyfluorane, enflurane, and the like. Unfortunately, chronic exposure to such agents, e.g. among anesthesiologists and other health care personnel, is correlated with higher rates of miscarriages, and psychomotor impairment.

Recently, the specter has arisen that organohalogen compounds formed inadvertently in the environment could be carcinogenic or otherwise toxic. About 1.1 million tons of chlorine are used annually for water purification. Water, of course, contains many organic impurities, some of natural origin and others anthropogenic. Inevitably some of these are chlorinated during treatment, which leads to the introduction into drinking water of a vast miscellany of organohalogen compounds, some of which are known to be carcinogenic, such as trichloroethylene. Other organohalogens are introduced into public water supplies, particularly aquifers, as pollutants by accidental release or mishandling of a variety of organic solvents used in industry.

Concern about the health effects of organohalogens in the environment has lead to the development of methods for detecting and monitoring their presence.

One such method is based on the reaction of halogenated hydrocarbons with pyridine or pyridine derivatives in an alkaline medium to yield highly colored products. It is known in the art that when a gem-polyhalogenated compound is heated with pyridine in a strongly alkaline medium, such as in the presence of sodium or potassium hydroxide, a product forms which is both chromogenic and fluorescent.

This reaction scheme, shown in Equation I below,

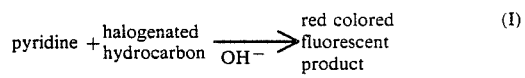

is known as the Fujiwara reaction (K. Fujiwara, Sitzfer, Abhandl. Naturforsch. Ges. Rostock., 6, 33, (1914); G. A. Lugg, Anal. Chem., 38, 1532 (1966); T. Uno et al., Chem. Pharm. Bull., 30, 1876 (1982). The Fujiwara reaction has become the classical method for the detection of halogenated hydrocarbons in the liquid phase. However, for a quantitative measure of halogenated hydrocarbons in a test solution or sample, the Fujiwara reaction presents some problems, due to the insolubility of pyridine in reagents normally used to generate the necessary alkalinity, and the difficulty in being able to control the rate of diffusion of the OH— ion from the aqueous phase into the organic pyridine phase.

More often, the reaction consists of a two-phase procedure whereby the gem-polyhalogenated compound, pyridine and aqueous sodium or potassium hydroxide are combined, mixed, and heated for a predetermined length of time until an intensely red color develops, which is due to the chromogenic product. The pyridine phase is then separated from the alkaline phase by conventional methods. Absorption spectra of the colored product are measured thereafter. The amount of the chromogenic product formed is dependent on the amount and rate of diffusion of the hydroxide ion into the pyridine phase of the mixture as well as the concentration of gem-polyhalogenated hydrocarbon in the sample solution. Since this diffusion is difficult to control, reproducibility of measurements becomes extremely difficult and unpredictable.

A one phase procedure using pyridine-water-sodium hydroxide has also been employed to avoid the pitfalls of the two phase method (G. A. Lugg, supra). However, current single phase procedures result in much lower sensitivity because only a small fraction of the single phase reaction mixture can consist of water, which is required for creating the necessary basicity from dissolved alkali metal hydroxides. The lower concentration of hydroxyl radicals results in lower amounts of chromogenic indicator for detecting the presence of gem-polyhalogenated hydrocarbons.

Apart from the particular analytical method used to detect organohalogens in a liquid sample, additional problems exist with currently used methods for monitoring groundwater contaminants. Typically such methods now involve digging well fields having numerous boreholes large enough to admit sample collectors, which are then brought back to a laboratory for analysis, e.g., Young and Baxter, "Overview of Methods for Ground Water Investigations," in Ward, et al., Eds., *Ground Water Quality*, pgs. 219-240 (John Wiley & Sons, New York, 1981).

Fiber optic sensing devices currently being developed offer a way to avoid the expense associated with currently available monitoring systems, e.g. Hirschfeld, et al, "Feasibility of Using Fiber Optics for Monitoring Groundwater Contaminants," *Optical Engineering*, Vol. 22, pgs. 527-531 (1983). In particular, many miniature in situ optical probes can be distributed throughout the region to be monitored, and connected by fiber optics to a centrally located instrument for spectroscopic analysis. Thus remote real-time continuous monitoring is possible with such a system.

Miller, et al, in co-pending U.S. patent application Ser. No. 721,150, filed Apr. 8, 1985, now U.S. Pat. No. 4,666,672 issued May 19, 1987, disclose a fiber optic sensor which uses a two phase Fujiwara reaction for detecting halogenated hydrocarbons. In the preferred embodiment the two phases are held contiguously inside a capillary tube attached to the end of a fiber optic such that an interface between the two phases is formed adjacent to the end of the fiber optic.

The position of the end of the fiber optic with respect to the interface is critical to the reliable and repeatable operation of the sensor. However, because the aqueous phase has a different density than the organic phase, any change in position of the capillary tube causes the interface to change position with respect to the end of the fiber optic which, in turn, unpredictably alters the optical signal collected by the fiber optic.

Clearly it would be advantageous to have an optical probe for detecting halogenated hydrocarbons based on the Fujiwara reaction which is not limited by the problems associated with a two phase reaction system.

SUMMARY OF THE INVENTION

The invention includes a new method for detecting gem-polyhalogenated hydrocarbons based on an impoved single phase Fujiwara reaction. The invention also includes apparatus which utilizes the improved single phase Fujiwara reaction for remote fluorometric detection of gem-polyhalogenated hydrocarbons over optical fibers. The improvement to the Fujiwara reaction involves mixing the organic phase reactants with a hindered nitrogen base and water to form a single phase system containing high concentrations of hydroxyl ions. The hindered nitrogen base is selected from the group defined by the formula:

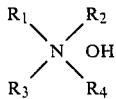

wherein $R_1$, $R_2$, $R_3$, and $R_4$ are each selected from the group consisting of lower alkyl, hydroxy-substituted lower alkyl, phenyl, lower alkyl-substituted phenyl, and phenyl-substituted lower alkyl. As used herein, the term "lower alkyl" refers to branched or unbranched alkyl having between 1–4 carbon atoms. More preferably, $R_1$, $R_2$, $R_3$, and $R_4$ are each selected from the group consisting of unbranched lower alkyl, hydroxyl-substituted unbranched lower alkyl, phenyl, and benzyl. In still further preference, the hindered nitrogen base is selected from the group consisting of benzyltrimethylammonium hydroxide, 2-hydroxyethyltrimethylammonium hydroxide, methyltributylammonium hydroxide, phenyltrimethylammonium hydroxide, tetrabutylammonium hydroxide, tetramethylammonium hydroxide, tetraethylammonium hydroxide, and tetrapropylammonium hydroxide. Most preferably, the hindered nitrogen base is selected from the group consisting of tetraethylammonium hydroxide, tetrapropylammonium hydroxide, and methyltributylammonium hydroxide.

The method of the invention employs the following general reaction:

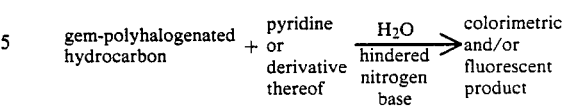

The prefix "gem-" as used herein in reference to polyhalogenated hydrocarbons means that at least one carbon is di-, tri-, or tetra-substituted with halogen atoms. Preferably, the halogen substitutes of the gem-polyhalogenated hydrocarbons are chloro-, bromo-, or iodo-; more preferably, they are bromo- or chloro-; and most preferably they are chloro-.

A major constituent of the reaction is pyridine or one of its derivatives. It is believed that the pyridine ring (or the ring of a derivative) is cleaved and combines with the halogenated hydrocarbon and one or more hydroxyls to form a conjugated straight chain product which can be detected colorimetrically or fluorimetrically, e.g., Uno, et al., "The Fujiwara Reaction: Isolation and Structural Investigation of the Reaction Product from Chloroform," *Chem. Pharm. Bull.*, Vol. 30, pgs. 1876–1879 (1982); Uno, et al., "Mechanism of the Fujiwara Reaction: Structural Investigation of Reaction Products from Benzotrichloride," *J. Org. Chem.*, Vol. 46, pgs. 3175–3178 (1981); Keith, et al., "An Improved Procedure for Application of the Fujiwara Reaction in the Determination of Organic Halides," *Analyst*, Vol. 99, pgs. 652–656 (1974). Preferably, the pyridine derviative for use with the reaction consist of a monosubstituted pyridine. More preferably, the pyridine derivatives are selected from the group consisting of methylpyridine, nicotinamide, and nicotinic acid. Most preferably, the pyridine derivative is 3-picoline (3-methylpyridine).

Gem-polyhalogenated hydrocarbons detectable by the method of the invention include chloroform, bromoform, iodoform, trichloroacetic acid, 2-trichloromethylpropan-2-ol, 1,1,2,2-tetrachloroethane, tribromoethylene, carbon tetrachloride, carbon tetrabromide, trichloroethylene, dichloroacetic acid, 1,1,1-trichloroethane, chloral hydrate, tetrachloroethane, tetrachloroethylene, pentachloroethane, chloral betaine, bromodichloromethane, chlorodibromomethane, and the like. Preferably, the method of the invention is for detecting gem-polychlorohydrocarbons such as those listed above. More preferably, the method of the invention is for detecting trichloroethylene, chloroform, tetrachloroethylene, 1,1,1-trichloroethane, 1,1,2,2-tetrachloroethane, 1,1-dichloroethylene, and the like.

Preferably, the method of the invention is carried out by an optrode. As used herein, the term "optrode" refers to a fiber optic together with means for holding the reactants of the invention adjacent to an end of the fiber optic, and means for separating the reactants from a sample fluid containing gem-polyhalogenated hydrocarbons. The preferred form of optrode comprises a fiber optic through which light from an illumination beam is transmitted from a first end to a second end, a tube sealingly attached to the second end of the fiber optic, reactants of the invention disposed in the tube so that they contact the second end of the fiber optic, and means operationally associated with the end of the tube distal to the second end of the fiber optic for separating the reactants of the invention from the sample fluid.

Preferably, the latter means is a bubble, a membrane, or both a bubble and a membrane.

The invention also includes apparatus for operating the optrode. Such apparatus comprises an optrode and an associated light source for causing the reaction product to fluoresce by way of the fiber optic, means associated with the first end of the fiber optic for separating the illumination beam of the associated light source from fluorescent light generated by the reaction product and collected by the fiber optic, and detection means for collecting and analyzing the separated fluorescence.

DETAILED DESCRIPTION OF THE INVENTION

Figure 1:
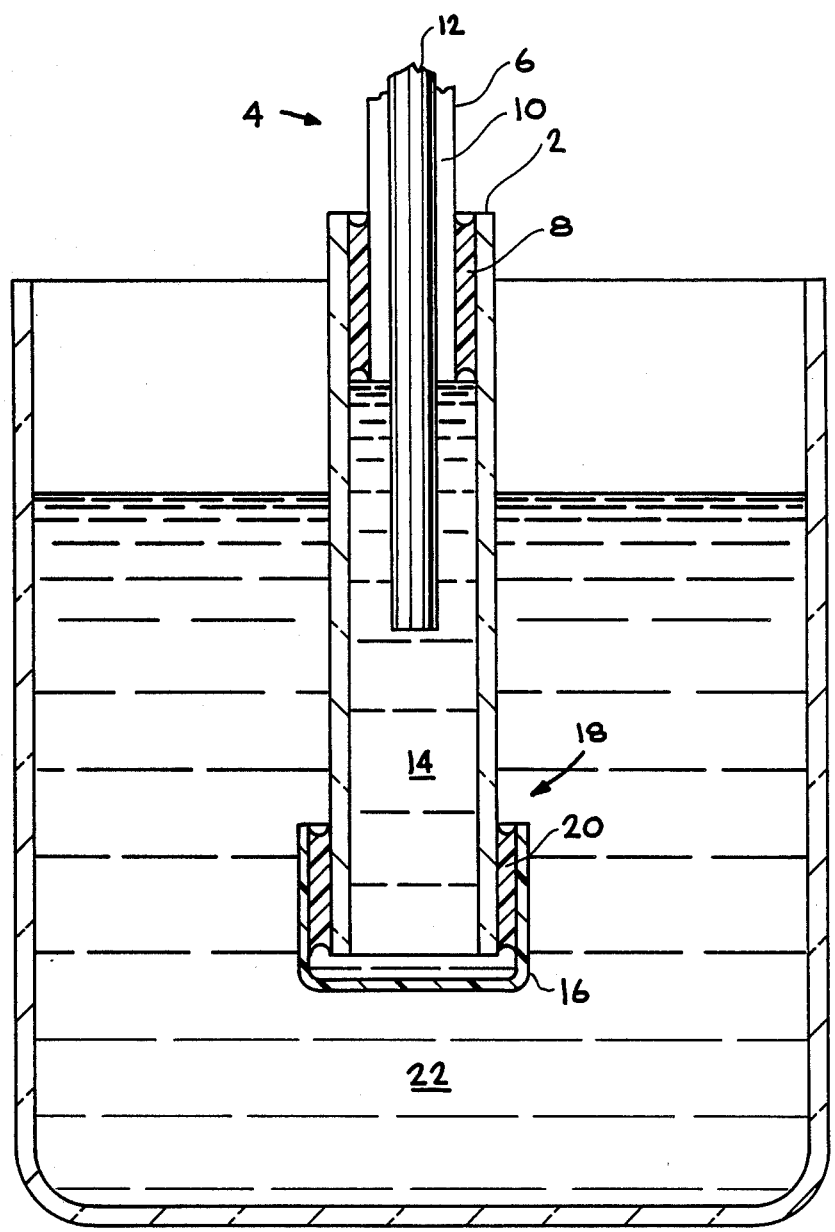
FIG. 1 is a cross sectional view of an embodiment of the optrode, employing a membrane for separating the reaction mixture from the sample fluid.

The invention includes method and apparatus for detecting gem-polyhalogenated hydrocarbons based on a single phase Fujiwara reaction utilizing the following class hindered nitrogen bases as a source of hydroxyl ions:

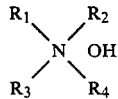

wherein $R_1$, $R_2$, $R_3$, and $R_4$ are each selected from the group consisting of lower alkyl, hydroxy-substituted lower alkyl, lower alkyl-substituted phenyl, and phenyl-substituted lower alkyl. Most preferably, the hindered nitrogen base is selected from the group consisting of tetraethylammonium hydroxide, tetrapropylammonium hydroxide, and tetrabutylammonium hydroxide.

The method of the invention is carried out by the following steps. First, pyridine or a derivative thereof is combined with an aqueous solution of a hindered nitrogen base to form a reaction mixture in which the concentration of pyridine or its derivative is (1) in the range of between about 60–96 percent (vol/vol), with the remaining volume consisting of the aqueous solution, and (2) in which the hindered nitrogen base is present in the reaction mixture at a concentration within the range of between about 0.01–0.05 molar. More preferably, the reaction mixture consists of pyridine or its derivative at a concentration in the range of 80–92 percent, with the remaining volume consisting of the aqueous solution and the hindered nitrogen base being present at a concentration within the range of between about 0.01–0.05 molar. The precise concentrations of reactants within these ranges depends in part on the particular hindered nitrogen base selected, reaction temperature, and on the application. As indicated by the examples given below, the hindered nitrogen base in some cases degrades the fluorescent and/or colorimetric reaction product. The rate of degradation depends on the concentration of the hindered nitrogen base. Thus, in some situations, for example when the reaction mixture is used with an optrode, a trade off must be made between faster response time of the optrode to the presence of gem-polyhalogenated hydrocarbons (e.g., higher concentrations of hindered nitrogen base) and the longevity of the optrode (which is prolonged by lower concentrations of the hindered nitrogen base). Optimal concentrations for particular applications can be established by routine experimentation. Particular reaction temperatures are not critical to the method; however, the reaction generally proceeds faster at higher temperatures. If a particular application permits control, reaction temperature is preferably in the range of between about 20°–80° C., and more preferably in the range of between about 40°–70° C. Again, in some applications, the need for an optrode with a longer life may require operation at lower temperatures.

Generally, the color of the reaction product appears bright red to reddish brown. The product is also fluorescent. The optimal absorption bands or excitation bands for colorimetric or fluorimetric detection depends on the particular reactants employed, and the gem-polyhalogenated hydrocarbon present.

Preferably the method of the invention is used in conjunction with an optrode. FIG. 1 is a cross sectional view of one embodiment of an optrode of the invention immersed in a sample solution 22. Tube 2 is sealingly attached to second end 4 of fiber optic 6, for example by an adhesive 8 (as shown), by welding, or the like. An exemplary adhesive is EPO-TEK 301 epoxy, available from Epoxy Technology, Inc. (Billerica, MA). Preferably, cladding 10 of fiber optic 6 is stripped away from core 12 of fiber optic 6. Core 12 then extends into reaction mixture 14. The cladding is stripped from the core to prevent later separation caused by the reactants. Such separation could cause unpredictable variations in signal over the life of the optrode. Membrane 16 is sealingly attached to distal end 18 of tube 2 with an adhesive 20, or the like, such as Light-weld No. 415, a UV light curing adhesive, available from American Chemical and Engineering (Torrington, CN). Preferably, membrane 16 is semipermeable, being impermeable to water, the hindered nitrogen base, and pyridine or derivatives thereof, but permeable to the gem-polyhalogenated hydrocarbons being detected. Exemplary membrane materials include thin paraffin films, such as Parafilm, mylar, zeflour, polycarbonate films, or the like. In some cases, it may be necessary to modify membrane 16 to permit attachment to tube 2. Membrane 16 serves to separate reaction mixture 14 from sample solution 22, and keeps reaction mixture 14 sequestered in tube 2, thereby controlling the relative concentrations of the reactants. Secondarily, membrane 16 serves to select gem-polyhalogenated hydrocarbons for detection.

Figure 2:
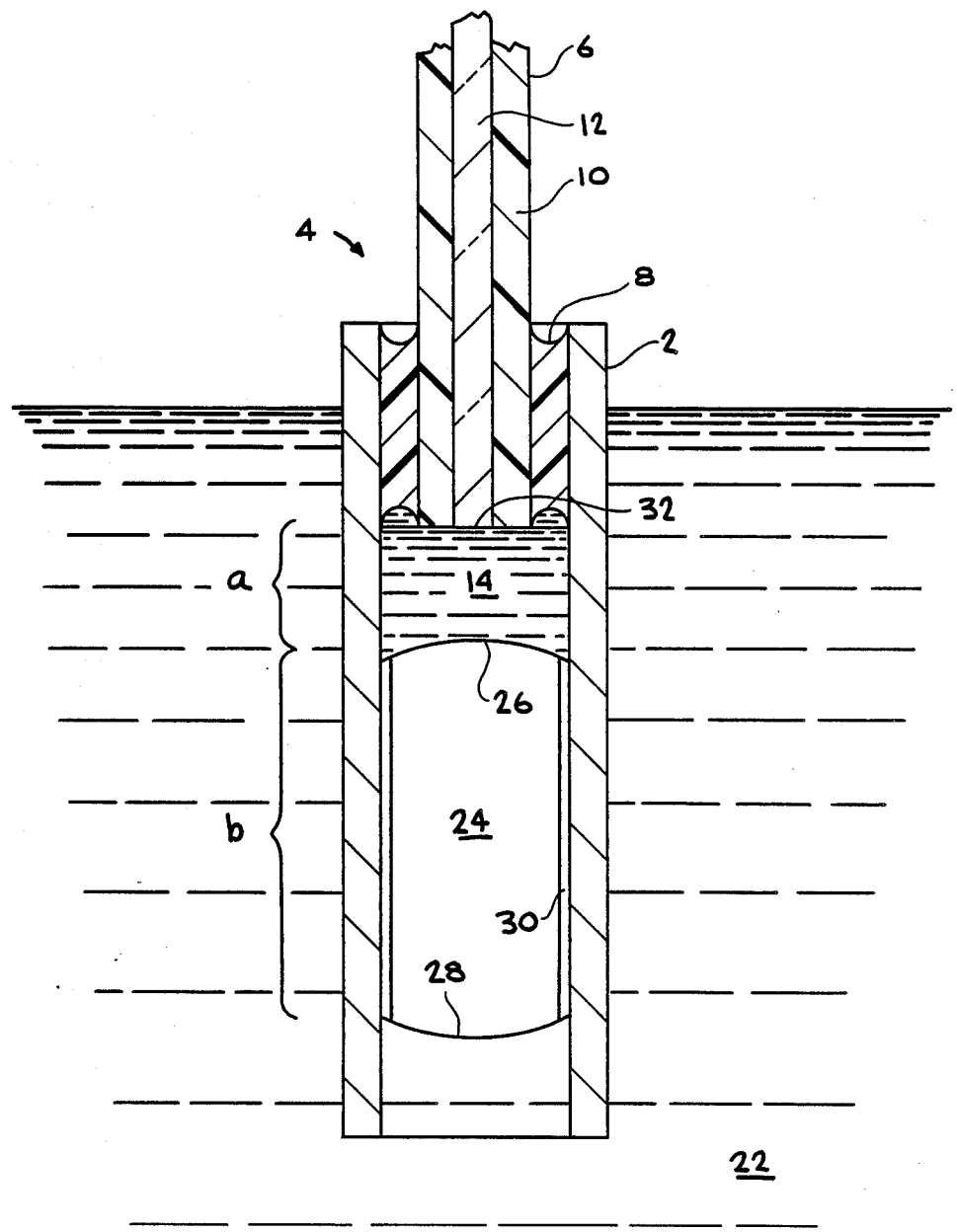
FIG. 2 is a cross sectional view of an embodiment of the optrode, employing a bubble for separating the reaction mixture from the sample fluid.

FIG. 2 is a cross sectional view of an embodiment of the optrode which employs a bubble. Numbers in FIG. 2 which are the same as those in FIG. 1 represent the same elements as those in FIG. 1. Here, tube 2 causes the formation of bubble 24 which separates reaction mixture 14 from sample fluid 22. Bubble 24 is defined by liquid-air interfaces 26 and 28. Preferably, the inner wall of tube 2 is coated with hydrophobic coating 30 to assist the formation of bubble 24 whenever tube 2 is immersed in an aqueous solution. If tube 2 is glass, such a coating may be applied by treatment with polymethylhydrosiloxane, which is available from Petrarch Systems, Inc. (Bristol, PA), or other procedures for siliconizing glassware, e.g., Schlief et al., *Practical Methods in Molecular Biology* (Springer-Verlag, New York, 1981), page 174. The linear dimensions indicated by "a" and "b" in FIG. 2 are, respectively, the distance between end face 32 of fiber optic 6 and liquid-air interface 26, and the distance between liquid-air interface 28 and liquid-air interface 26. The exact values of these dimensions are not crucial to the invention; however, the response time of a sensor employing the present invention depends on the rate of diffusion of the gases or volatile components of interest across distance "b", and on the rate of diffusion of the gases or volatile components within reaction mixture 14.

Preferably, in the case of the embodiment of FIG. 2, "a" is as small as possible consistent with the generation of a detectable signal from reaction mixture 14.

Other means are available for forming bubble 24, e.g., such as those disclosed by Hirschfeld in co-pending U.S. patent application Ser. No. 820,122, filed Jan. 21, 1986, entitled "Gas-Sensing Optrode."

Figure 3:
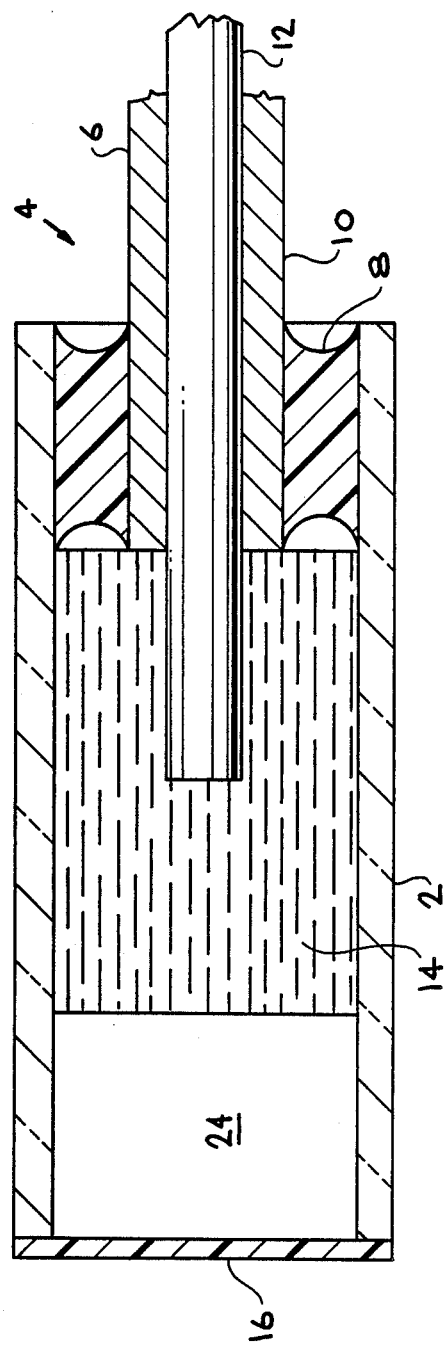
FIG. 3 is a cross sectional view of an embodiment of the optrode, employing both a bubble and a membrane for separating the reaction mixture from the sample fluid.

FIG. 3 is a cross sectional view of an embodiment of the optrode employing both a membrane and a bubble. Again, like numbers to those of FIGS. 1 and 2 indicate identical elements.

Figure 4:
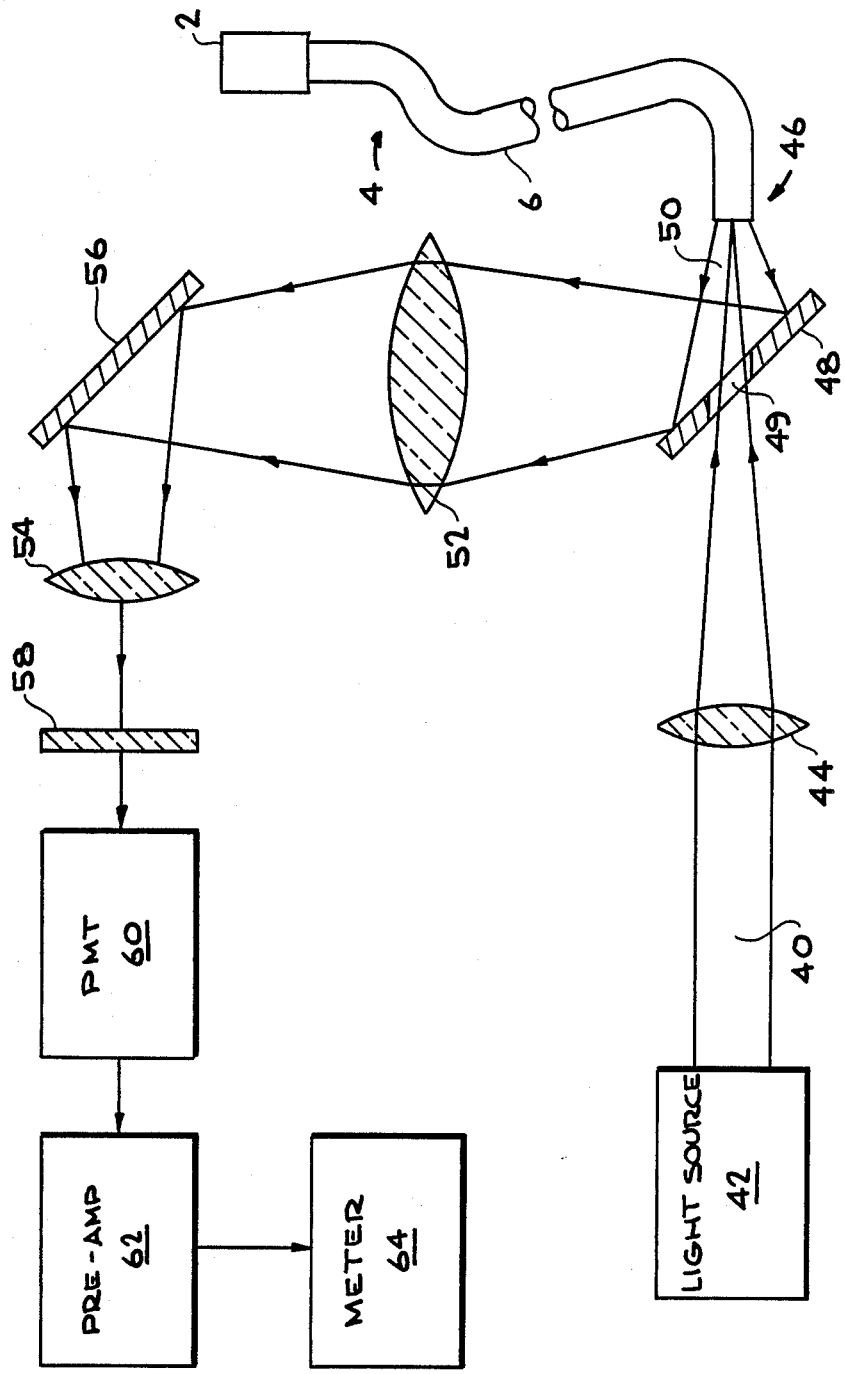
FIG. 4 diagrammatically illustrates one embodiment of the apparatus for operating the optrode of the invention.

FIG. 4 diagrammatically illustrates preferred apparatus for operating the optrode of the invention. Illumination beam 40 generated by light source 42 is focused by lens 44 and directed to first end 46 of fiber optic 6. Preferably, light source 42 is a laser operating at a wavelength suitable for inducing the fluorescent product contained in tube 2 to fluoresce. Alternatively, light source 42 can comprise a mercury or xenon arc lamp with suitable filters. The focal length of lens 44 is relatively long so that the angle of incidence of illumination beam 40 as it enters fiber optic 6 is within the acceptance angle of the fiber optic. Fiber optic 6 is preferably a step index type communications fiber optic, such as a Valtec PC-10 (Valtec Corp., West Boylstron, MA), or the like; although this is not a critical requirement of the invention, and other types of fiber optics can be used.

Illumination beam 40 exits fiber optic 6 at second end 4 so that the fluorescent product contained in tube 2 is caused to fluoresce. A portion of the fluorescence is collected by fiber optic 6 at second end 4 and transmitted to first end 46. Adjacent to first end 46, apertured mirror 48 having aperture, 49 separates the "outgoing" illumination beam 40 from the "incoming" fluorescent signal 50. Apertures mirror 48 is an example of a separation means referred to above. Another example is a dichroic mirror. Lens 52 collects fluorescent signal 50 and focuses it on collimating lens 54 via mirror 56. Fluorescent signal 50 then passes through band-pass filter 58 and is collected by photomultiplier tube 60. Band-pass filter 58 is chosen to restrict the light incident on the photomultiplier tube 60 to that which has wavelengths corresponding to those emitted by the fluorescent product. The output signal from photomultiplier tube 60 is amplified by preamplifier 62. The output signal of preamplifier 62 can be read directly on meter 64 or like readout means, to give a measure proportional to the fluorescence generated by the fluorescent product.

Operation of the optrode of the invention can also be implemented by apparatus disclosed in U.S. Pat. Nos. 4,509,370; 4,542,987; and 4,447,546; which patents are incorporated by reference for those disclosures.

The following examples serve to illustrate the present invention. The concentrations of reagents, temperatures, and values of other variable parameters are only to exemplify the application of the present invention, and are not to be considered as limitations thereof.

EXAMPLE I

Detection of Chloroform by Reaction with Pyridine and Tetrabutylammonium Hydroxide To 3.0 ml of reaction mixture (90% (v/v) pyridine, 6% water, 4% tetrabutyl ammonium hydroxide) was added 30 microliters of a 1000 microgram/ml solution of $CHCl_3$ to give about 10 ppm solution of $CHCl_3$. The resulting mixture was placed in the quartz sample cuvette of a Varian model DMS-1000 spectrophotometer. The following relative absorbance over time was obtained at 525 nm.

| Time (min.) | $A_{525}$ | Time (min.) | $A_{525}$ |
|---|---|---|---|
| 1 | .114 | 8 | .131 |
| 2 | .122 | 9 | .130 |
| 3 | .126 | 10 | .130 |
| 4 | .128 | 16 | .124 |
| 5 | .130 | 20 | .119 |
| 6 | .131 | 50 | .084 |
| 7 | .131 | | |

In a second run, 3.0 ml. of reaction mixture (2.4 ml pyridine and 0.6 ml of 0.15M tetrabutylammonium hydroxide) was added to 30 microliters of a 1000 microgram/ml solution of $CHCl_3$ to give about a 10 ppm solution of $CHCl_3$. The resulting mixture was placed in the quartz sample cuvette of a Varian model DMS-100 spectrophotometer. The following relative absorbance over time was obtained at 525 nm.

| Time (min.) | $A_{525}$ | Time (min.) | $A_{525}$ |
|---|---|---|---|
| 0.5 | .126 | 5.5 | .144 |
| 1.0 | .133 | 6.0 | .144 |
| 1.5 | .136 | 6.5 | .145 |
| 2.0 | .138 | 7.0 | .145 |
| 2.5 | .139 | 7.5 | .146 |
| 3.0 | .140 | 8.0 | .146 |
| 3.5 | .141 | 8.5 | .146 |
| 4.0 | .142 | 9.0 | .147 |
| 4.5 | .142 | 9.5 | .147 |
| 5.0 | .143 | 10.0 | .147 |

In a third run, to 3.0 ml of a reaction mixture (0.6 ml 0.15M tetrabutylammonium hydroxide, 0.3 ml distilled water, 2.1 ml pyridine) was added 30 microliters of 1000 microgram/ml solution of $CHCl_3$ to give about a 10 ppm solution of $CHCl_3$. The absorbance over time of the resulting mixture was determined as above:

| Time (min.) | $A_{525}$ | Time (min.) | $A_{525}$ |
|---|---|---|---|
| 1 | .087 | 8 | .350 |
| 2 | .136 | 9 | .374 |
| 3 | .182 | 10 | .396 |
| 4 | .222 | 15 | .484 |
| 5 | .258 | 20 | .536 |
| 6 | .292 | 30 | .582 |
| 7 | .322 | 80 | .520 |

EXAMPLE II

Detection of Chloroform by Reaction with Pyridine and Tetrapropylammonium Hydrodroxide To 3.0 ml of reaction mixture (90% (v/v) aqueous pyridine, 0.05M tetrapropylammonium hydroxide) was added 30 microliters of a 1000 microgram/ml solution of $CHCl_3$ to give about a 10 ppm solution of $CHCl_3$. The absorbance over time of the resulting mixture was recorded as in Example I:

| Time (hrs.) | $A_{525}$ | Time (min.) | $A_{525}$ |
|---|---|---|---|
| .033 | .039 | 1.75 | .378 |
| .10 | .060 | 2.75 | .451 |
| .20 | .094 | 3.75 | .482 |
| .30 | .127 | 4.75 | .503 |
| .40 | .158 | 5.75 | .518 |
| .50 | .182 | 6.75 | .530 |
| .60 | .209 | 7.25 | .533 |
| .70 | .234 | 7.75 | .540 |
| .80 | .252 | | |
| .90 | .271 | | |
| 1.2 | .32 | | |

In a second run, to 3.0 ml of a reaction mixture (90% (v/v) aqueous pyridine, 0.04M tetrapropylammonium hydroxide) was added 30 microliters of a 1000 microgram/ml solution of $CHCl_3$ to give about a 10 ppm solution of $CHCl_3$. The absorbance over time was recorded as in Example I at both 525 nm and 367 nm:

| Time (hrs.) | $A_{525}$ | $A_{367}$ | Time (hrs.) | $A_{525}$ | $A_{367}$ |
|---|---|---|---|---|---|
| .1 | .372 | 1.009 | .9 | .356 | 1.327 |
| .2 | .437 | 1.172 | 1.0 | .351 | 1.339 |
| .3 | .443 | 1.219 | 1.2 | .324 | 1.358 |
| .4 | .434 | 1.243 | 1.3 | .313 | 1.369 |
| .5 | .421 | 1.263 | 1.4 | .301 | 1.379 |
| .6 | .407 | 1.283 | 1.6 | .279 | 1.394 |
| .7 | .393 | 1.301 | 1.8 | .259 | 1.410 |
| .8 | .379 | 1.316 | 2.0 | .240 | 1.424 |

In a third run, to 3.0 ml of a reaction mixture (90% (v/v) aqueous pyridine, 0.03M tetrapropylammonium hydroxide) was added 30 microliters of a 1000 microgram/ml solution of $CHCl_3$ to give about a 10 ppm solution of $CHCl_3$. The absorbance over time of the resulting mixture was recorded as in Example I for both 525 nm and 367 nm:

| Time (hrs.) | $A_{525}$ | $A_{367}$ | Time (hrs.) | $A_{525}$ | $A_{367}$ |
|---|---|---|---|---|---|
| .1 | .24 | .55 | 1.6 | .522 | 1.29 |
| .2 | .36 | .76 | 1.7 | .511 | 1.30 |
| .3 | .44 | .90 | 1.8 | .500 | 1.306 |
| .4 | .50 | 1.00 | 1.9 | .489 | 1.313 |
| .5 | .53 | 1.07 | 2.0 | .478 | 1.322 |
| .6 | .55 | 1.12 | 2.1 | .467 | 1.331 |
| .7 | .57 | 1.15 | 2.2 | .487 | 1.339 |
| .8 | .572 | 1.18 | 2.4 | .436 | 1.355 |
| .9 | .570 | 1.20 | 2.5 | .426 | 1.363 |
| 1.0 | .564 | 1.21 | 2.6 | .417 | 1.371 |
| 1.1 | .556 | 1.22 | 2.7 | .407 | 1.378 |
| 1.2 | .550 | 1.23 | 2.8 | .397 | 1.386 |
| 1.3 | .545 | 1.25 | 2.9 | .388 | 1.393 |
| 1.4 | .542 | 1.27 | 3.0 | .379 | 1.400 |
| 1.5 | .533 | 1.28 | | | |

In a fourth run, to 3.0 ml of a reaction mixture (0.2M tetrapropylammonium hydroxide, 90% (v/v) aqueous pyridine) was added 30 microliters of a 1000 microgram/ml solution of $CHCl_3$ to give about a 10 ppm solution of $CHCl_3$. The absorbance over time of the resulting mixture was recorded as in Example I for 525 nm:

| Time (min.) | $A_{525}$ | Time (min.) | $A_{525}$ |
|---|---|---|---|
| .1 | .11 | 1.4 | .484 |
| .2 | .18 | 1.5 | .483 |
| .3 | .25 | 1.6 | .481 |
| .4 | .30 | 1.7 | .479 |
| .5 | .34 | 1.8 | .474 |
| .6 | .38 | 1.9 | .470 |
| .7 | .42 | 2.0 | .465 |
| .8 | .44 | 2.1 | .460 |
| .9 | .46 | 2.2 | .454 |
| 1.0 | .47 | 2.3 | .449 |
| 1.1 | .48 | 2.4 | .443 |
| 1.2 | .48 | 2.5 | .437 |
| 1.3 | .483 | | |

In a fifth run, to 3.0 ml of a reaction mixture (0.01M tetrapropyl ammonium hydroxide, 90% (v/v) aqueous pyridine) was added 30 microliter of a 1000 microgram/ml solution of $CHCl_3$ to give about a 10 ppm solution of $CHCl_3$. The absorbance over time of the resulting solution was recorded as in Example I for 525 nm:

| Time (min.) | $A_{525}$ | Time (min.) | $A_{525}$ |
|---|---|---|---|
| .1 | .07 | 1.0 | .43 |
| .2 | .11 | 1.2 | .50 |
| .3 | .15 | 1.4 | .55 |
| .4 | .19 | 1.6 | .59 |
| .5 | .23 | 1.8 | .62 |
| .6 | .27 | 2.0 | .64 |
| .7 | .31 | 2.2 | .657 |
| .8 | .35 | 2.4 | .663 |
| .9 | .39 | | |

EXAMPLE III

Detection of Chloroform by Reaction with Pyridine and Tetraethylammoium Hydroxide To 3.0 ml of a reaction mixture (0.02M tetraethylammonium hydroxide, 90% (v/v) aqueous pyridine) was added 30 microliters of a 1000 microgram/ml solution of $CHCl_3$ to give about a 10 ppm solution of $CHCl_3$. The absorbance over time of the resulting mixture was recorded as above for 525 nm:

| Time (min.) | $A_{525}$ | Time (min.) | $A_{525}$ |
|---|---|---|---|
| .1 | .10 | .7 | .244 |
| .2 | .14 | .8 | .255 |
| .3 | .165 | .9 | .263 |
| .4 | .190 | 1.0 | .269 |
| .5 | .210 | 1.1 | .272 |
| .6 | .230 | 1.2 | .276 |

The disclosure of the foregoing embodiments and examples of the invention have been prsented for purposes of illustration and description. They are not intended to be exhaustive or to limit the invention to the precise form disclosed, and obviously many modifications and variations are possible in light of the above teaching. The embodiments and examples were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

It is claimed:

1. A method of detecting gem-polyhalogenated hydrocarbons, the method comprising the steps of:
combining a pyridine reaction constituent selected from the group consisting of pyridine and derivatives thereof with an aqueous solution of a hindered nitrogen base to form a reaction mixture, the reaction mixture comprising the pyridine reaction constituent at a concentration in the range of between 60 to about 96 percent by volume of the reaction mixture, the remaining volume comprising the aqueous solution such that the hindered nitrogen base is present in the reaction mixture at a concentration in the range of between about 0.01–0.05 molar, the hindered nitrogen base being selected from the group consisting of the formula:

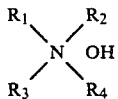

wherein $R_1$, $R_2$, $R_3$, and $R_4$ are substituents independently selected from the group consisting of lower alkyl, hydroxy-substituted lower alkyl, phenyl, lower alkyl-substituted phenyl, and phenyl-substituted lower alkyl;
reacting the reaction mixture with a gem-polyhalogenated hydrocarbon to form a reaction product which is at least one of fluorescent and chromogenic;
illuminating the reaction product with an illumination beam; and
detecting the gem-polyhalogenated hydrocarbon by at least one of the fluorescence and absorbance of the reaction product.

2. The method of claim 1 wherein said reaction mixture consists of pyridine reaction constituent at a concentration in the range of between about 80 to about 92 percent by volume of the reaction mixture, and said substituents $R_1$, $R_2$, $R_3$, and $R_4$ are each lower alkyl.

3. The method of claim 2 wherein said substituents $R_1$, $R_2$, $R_3$, $R_4$ are each lower alkyl selected from the group consisting of n-ethyl, n-propyl, and n-butyl.

4. The method of claim 3 wherein said pyridine reaction constituent is selected from the group consisting of pyridine, 3-picoline, nicotinamide, and nicotinic acid.

5. The method of claim 4 wherein said pyridine reaction constituent is pyridine.

6. The method of claim 5 wherein said gem-polyhalogenated hydrocarbon is selected from the group consisting of trichloroethylene, chloroform, 1,1,1-trichloroethane, 1,1,2,2-tetrachloroethane, and 1,1-dichloroethylene.

7. The method of claim 6 wherein said step of detecting includes measuring the absorbance of said reaction product.

8. An optrode for monitoring the concentration of gem-polyhalogenated hydrocarbons in a sample fluid, the optrode comprising:
a fiber optic through which an illumination beam from an associated light source is transmitted from a first end of the fiber optic to a second end of the fiber optic;
a reaction mixture held adjacent to the second end of the fiber optic such that light from the illumination beam emanating from the second end of the fiber optic illuminates a portion of the reaction mixture causing it to produce an optical signal related to the concentration of gem-polyhalogenated hydrocarbons when the second end of the fiber optic is immersed in a sample fluid, the reaction mixture comprising an aqueous solution of a pyridine reaction constituent selected from the group consisting of pyridine and derivatives thereof at a concentration in the range of between about 60 to about 96 percent by volume of the reaction mixture, and a hindered nitrogen base at a concentration in the range of between about 0.01 to 0.05 molar, the hindered nitrogen base being selected from the group consisting of the formula

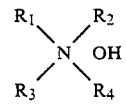

wherein $R_1$, $R_2$, $R_3$, and $R_4$ are substituents independently selected from the group consisting of lower alkyl, hydroxy-substituted lower alkyl, phenyl, lower alkyl-substituted phenyl, and phenyl-substituted lower alkyl; and
means attached to the second end of the fiber optic for holding the reaction mixture adjacent the second end of the fiber optic and for separating the reaction mixture from a sample fluid whenever the second end of the fiber optic is immersed in a sample fluid.

9. The optrode of claim 8 wherein said means for holding and separating comprise bubble forming means.

10. The optrode according to claim 9 wherein said bubble forming means is a tube coaxially attached to said second end of said fiber optic such that an airtight seal is formed and such that said reaction mixture is enclosed by the tube.

11. The optrode of claim 10 wherein said pyridine reaction constituent is at a concentration in the range of between about 80 to about 92 percent, and said substituents $R_1$, $R_2$, $R_3$ and $R_4$ of said hindered nitrogen base are each lower alkyl.

12. The optrode of claim 11 wherein said substituents $R_1$, $R_2$, $R_3$, and $R_4$ of said hindered nitrogen base are each lower alkyl selected from the group consisting of n-ethyl, n-propyl, and n-butyl.

13. The optrode of claim 12 wherein said pyridine reaction constituent is selected from the set consisting of pyridine, 3-picoline nicotinamide, and nicotinic acid.

14. The optrode of claim 13 wherein said pyridine reaction constituent is pyridine.

15. An apparatus for monitoring the concentration of gem-polyhalogenated hydrocarbons in a sample fluid, the apparatus comprising:
a fiber optic through which an illumination beam from an associated light source is transmitted from a first end of the fiber optic to a second end of the fiber optic;
a reaction mixture held adjacent to the second end of the fiber optic such that light from the illumination beam emanating from the second end of the fiber optic illuminates a portion of the reaction mixture causing it to produce a fluorescent signal related to the concentration of gem-polyhalogenated hydrocarbons when the second end of the fiber optic is immersed in a sample fluid, the reaction mixture comprising an aqueous solution of a pyridine reaction constituent selected from the group consisting of pyridine and derivatives thereof at a concentration in the range of between about 60 to about 96 percent by volume of the reaction mixture, and a hindered nitrogen base at a concentration in the range of between about 0.01 to 0.05 molar, the hindered nitrogen base being selected from the group consisting of the formula

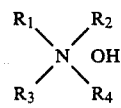

wherein $R_1$, $R_2$, $R_3$, and $R_4$ are substituents independently selected from the group consisting of lower alkyl, hydroxy-substituted lower alkyl, phenyl, lower alkyl-substituted phenyl, and phenyl-substituted lower alkyl;

means attached to the second end of the fiber optic for holding the reaction mixture adjacent the second end of the fiber optic and for separating the reaction mixture from a sample fluid whenever the second end of the fiber optic is immersed in a sample fluid;

means adjacent to the first end of the fiber optic for separating light from the associated light source from the fluorescent signal collected and transmitted by the fiber optic; and detection means adjacent to the separation means for collecting and analyzing the fluorescent signal generated by the reaction mixture.

16. The apparatus of claim 15 wherein said means for holding and separating comprise bubble forming means.

17. The apparatus of claim 16 wherein said bubble forming means is a tube coaxially attached to said second end of said fiber optic such that an airtight seal is formed and such that said reaction mixture is enclosed by the tube.

18. The apparatus of claim 17 wherein said pyridine reaction constituent is at a concentration in the range of between about 80 to about 92 percent, and said substituents $R_1$, $R_2$, $R_3$ and $R_4$ of said hindered nitrogen base are each lower alkyl.

19. The apparatus of claim 18 wherein said substituents $R_1$, $R_2$, $R_3$, and $R_4$ of said hindered nitrogen base are each lower alkyl selected from the group consisting of n-ethyl, n-propyl, and n-butyl.

20. The apparatus of claim 19 wherein said pyridine reaction constituent is pyridine.

* * * * *